United States Patent [19]

Straub et al.

[11] Patent Number: 5,410,055

[45] Date of Patent: Apr. 25, 1995

[54] 3-PHENYL-1,7-NAPHTHYRIDINE AND CINNOLINE-5-CARBOXYALDEHYDE INTERMEDIATES FOR MEDICAMENTS

[75] Inventors: Alexander Straub, Wuppertal; Jürgen Stoltefuss, Haan; Siegfried Goldmann, Wuppertal; Rainer Gross, Wuppertal; Martin Bechem, Wuppertal; Siegbert Hebisch, Wuppertal; Joachim Hütter, Wuppertal; Howard-Paul Rounding, Wuppertal, all of Germany

[73] Assignee: Bayer Aktiengesellschaft, Leverkusen, Germany

[21] Appl. No.: 230,579

[22] Filed: Apr. 21, 1994

Related U.S. Application Data

[62] Division of Ser. No. 6,592, Jan. 21, 1993, Pat. No. 5,364,855.

[30] Foreign Application Priority Data

Jan. 30, 1992 [DE] Germany .................. 42 02 526.5

[51] Int. Cl.⁶ ............... C07D 471/04; C07D 237/28; C07D 401/04; C07D 409/04
[52] U.S. Cl. ................................. 544/235; 546/122
[58] Field of Search ................. 544/235; 546/122

[56] References Cited

U.S. PATENT DOCUMENTS

| 3,485,847 | 12/1969 | Bossert et al. | 546/321 |
|---|---|---|---|
| 3,932,645 | 1/1976 | Meyer et al. | 514/334 |
| 4,038,399 | 7/1977 | Bossert et al. | 514/356 |
| 4,145,432 | 3/1979 | Sato | 514/356 |
| 4,248,873 | 2/1981 | Bossert et al. | 514/247 |
| 4,284,634 | 8/1981 | Satu | 514/344 |
| 4,707,479 | 11/1987 | Meyer et al. | 514/222 |
| 4,751,228 | 6/1988 | Kleinschroth et al. | 514/300 |
| 4,820,842 | 4/1989 | Anderson et al. | 546/135 |
| 5,100,900 | 3/1992 | Stoltefuss et al. | 514/314 |

FOREIGN PATENT DOCUMENTS

| 0186028 | 7/1986 | European Pat. Off. |
| 0452712 | 10/1991 | European Pat. Off. |
| 1173862 | 12/1969 | United Kingdom |

OTHER PUBLICATIONS

Straub, Synthetic Communications 23(3) pp. 365–372 (1993).

Collection of Czechoslovak Chemical Communications, 1/57/1992; "Synthesis and Calcium Antagonist Activity of Dialkyl . . . ", P. G. Baraldi et al., cover page and pp. 169–178.

Nature International Weekly Journal of Science, vol. 303, No. 5917, Jun. 9–15, 1983; Laser Processing of Silicon; "Novel dihydropyridines with positive inotropic action . . . ", M. Schramm et al, 5 pages.

Liebig's Ann. Chem., vol. 602, 1957, Seite 14, pp. 14–23; "Über Einige Umsetzungen des Nitroacetons", A. Dornow et al.

"Addition of Dinitrogen Tetroxide to Olefins. Part III. Propylene", N. Levy et al., pp. 1100–1104, (1946).

J. Org. Chem., vol. 20, 1955, pp. 927–936; "Aliphatic Nitro Ketones", C. D. Hurd et al.

(List continued on next page.)

Primary Examiner—Emily Bernhardt
Attorney, Agent, or Firm—Sprung Horn Kramer & Woods

[57] ABSTRACT

The invention relates to new 4-cinnolinyl- and 4-naphthyridinyl-dihydropyridines of the general formula I

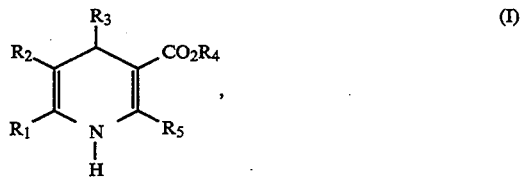

in which $R^1$ to $R^5$ have the meaning given in the description, to processes for their preparation and intermediates thereof and to their use in medicaments, in particular in compositions having positively inotropic action.

3 Claims, No Drawings

OTHER PUBLICATIONS

J. Physiol., 1965, vol. 180, pp. 529-541; "Coronary Flow Rate and Perfusion Pressure as Determinants of . . .", L. H. Opie.

Houben Weyl's Methods of Organic Chemistry, vol. VII/4, 1968, Seite 230, pp. 230-232; "Umsetzungen von Diketen mit Alkolholen, Phenolen und Mercaptanen", D. Borrmann.

J. Am. Chem., vol. 67, 1945, pp. 1017-1020; "Structure of β-Amino Derivatives of α,β-Unsaturated Lactones and Esters", S. A. Glickman et al.

Ann. Rev. Pharmacol., Toxicol., 1977, vol. 17, pp. 149-166; "Specific Pharmacology of Calcium in Myocardium, . . . ", A. Fleckenstein.

Journal of Medicinal Chemistry, 1978, vol. 21, No. 2, pp. 195-199; "Methyl-2(6)-nitro-and 3(5)-nitropyridinecarboxamides", Morisawa et al.

3-PHENYL-1,7-NAPHTHYRIDINE AND CINNOLINE-5-CARBOXYALDEHYDE INTERMEDIATES FOR MEDICAMENTS

This application is a division of application Ser. No. 08/006,592, filed on Jan. 21, 1992, now U.S. Pat. No. 5,364,855.

The invention relates to new 4-cinnolinyl- and 4-naphthyridinyl-dihydropyridines, to processes for their preparation and to their use in medicaments, in particular in compositions having positively inotropic action.

It is already known that 1,4-dihydropyridines have vasodilating properties and can be used as coronary agents and antihypertensives [cf. Brit. Patent 1,173,862 and 1,358,951; German Offenlegungsschrifts 2,629,892 and 2,752,820]. It is additionally known that 1,4-dihydropyridines cause an inhibition of the contractility of smooth and cardiac muscles and can be employed for the treatment of coronary and vascular diseases [cf. Fleckenstein, Ann. Rev. Pharmacol. Toxicol., 17, 149–166 (1977)].

It is additionally known that 3-nitro-dihydropyridines in general, in addition to a positively inotropic cardiac action, can show the disadvantage of an undesired constricting action on the coronary vessels [cf. Schramm et al., Nature 303, 535–537 (1983) and German Offenlegungsschrift 3,447,169].

With knowledge of the prior art, it was not foreseeable that the compounds according to the invention would have a contractility-enhancing, positively inotropic action on the heart muscle with substantially neutral or dilating vascular behaviour.

The invention relates to 4-cinnolinyl- and 4-naphthyridinyl-dihydropyridines of the general formula (I)

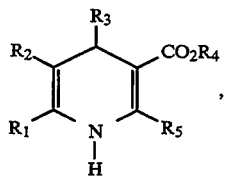

in which $R^1$ and $R^5$ are identical or different and represent straight-chain or branched alkyl having up to 8 carbon atoms, $R^2$ represents straight-chain or branched alkoxycarbonyl having up to 6 carbon atoms, which is optionally substituted by straight-chain or branched alkoxy having up to 4 carbon atoms, represents nitro or cyano, or $R^1$ and $R^5$ together form a lactone ring of the formula

$R^3$ represents a heterocyclic radical of the formula

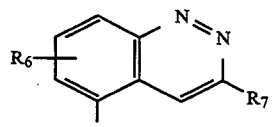

or

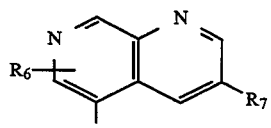

in which $R^6$ denotes hydrogen, halogen or straight-chain or branched alkyl or alkoxy each having up to 8 carbon atoms, $R^7$ denotes aryl having 6 to 10 carbon atoms, which is optionally substituted up to 2 times by identical or different substituents from the group consisting of halogen, nitro, cyano, trifluoromethyl, trifluoromethoxy, trifluoromethylthio, straight-chain or branched alkyl, alkoxy or alkoxycarbonyl each having up to 8 carbon atoms and carboxyl, or denotes pyridyl or thienyl, $R^4$ represents hydrogen, or represents straight-chain or branched alkyl, alkenyl, alkadienyl or alkinyl each having up to 10 carbon atoms, each of which is optionally substituted up to 2 times by identical or different substituents from the group consisting of trifluoromethyl, halogen, hydroxyl, carboxyl, cyano, nitro and phenoxy or by straight-chain or branched alkylthio, alkoxy, alkoxycarbonyl, acyl or acyloxy each having up to 8 carbon atoms or by phenoxy or phenyl, where the latter can for their part be substituted up to 2 times by identical or different halogen substituents or by straight-chain or branched alkyl or alkoxy each having up to 6 carbon atoms and their physiologically acceptable salts.

Physiologically acceptable salts can be salts of the compounds according to the invention with inorganic or organic acids. Preferred salts are those with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, lactic acid, benzoic acid, or methanesulphonic acid, ethanesulphonic acid, phenylsulphonic acid, toluenesulphonic acid or naphthalenedisulphonic acid.

The compounds according to the invention exist in stereoisomeric forms, which either behave as image and mirror image (enantiomers), or which do not behave as image and mirror image (diastereomers). The invention relates both to the antipodes and to the racemic forms as well as the diastereomer mixtures. Like the diastereomers, the racemic forms can also be separated in a known manner into the stereoisomerically uniform constituents (cf. E. L. Eliel, Stereochemistry of Carbon Compounds, McGraw Hill, 1962).

Preferred compounds of the general formula (I) are those
in which $R^1$ and $R^5$ are identical or different and represent straight-chain or branched alkyl having up to 6 carbon atoms, $R^2$ represents straight-chain or branched alkoxycarbonyl having up to 4 carbon atoms, which is optionally substituted by straight-chain or branched alkoxy having up to 3 carbon atoms, represents nitro or cyano, or $R^1$ and $R^2$ together form a lactone ring of the formula

$R^3$ represents a heterocyclic radical of the formula

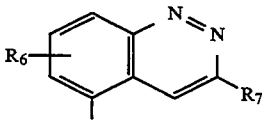

or

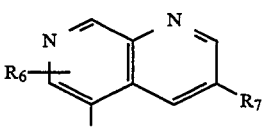

in which
$R^6$ denotes hydrogen, fluorine, chlorine or straight-chain or branched alkyl or alkoxy each having up to 2 carbon atoms, $R^7$ denotes phenyl which is optionally substituted by fluorine, chlorine, nitro, cyano or trifluoromethyl or by straight-chain or branched alkyl or alkoxy each having up to 6 carbon atoms, $R^4$ represents hydrogen, or represents straight-chain or branched alkyl or alkenyl each having up to 8 carbon atoms, each of which is optionally substituted by trifluoromethyl, fluorine, chlorine, hydroxyl, carboxyl, cyano or nitro or by straight-chain or branched alkylthio, alkoxy, alkoxycarbonyl, acyl or acyloxy each having up to 6 carbon atoms or by phenoxy or phenyl, and their physiologically acceptable salts.

Particularly preferred compounds of the general formula (I) are those
in which
$R^1$ and $R^5$ are identical or different and represent straight-chain or branched alkyl having up to 4 carbon atoms, $R^2$ represents straight-chain or branched alkoxycarbonyl having up to 3 carbon atoms, or methoxyethoxycarbonyl, or represents nitro or cyano, or $R^1$ and $R^2$ together form a lactone ring of the formula

$R^3$ represents a heterocyclic radical of the formula

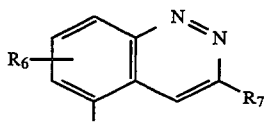

or

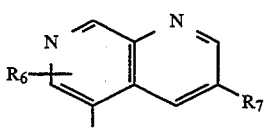

in which
$R^6$ denotes hydrogen, chlorine or methyl, $R^7$ denotes phenyl which is optionally substituted by fluorine, chlorine, nitro or trifluoromethyl or by straight-chain or branched alkyl or alkoxy each having up to 4 carbon atoms, $R^4$ represents hydrogen, or represents straight-chain or branched alkyl having up to 6 carbon atoms, which is optionally substituted by trifluoromethyl, hydroxyl, carboxyl or cyano or by straight-chain or branched alkoxycarbonyl, alkoxy or acyloxy each having up to 4 carbon atoms and their physiologically acceptable salts.

Additionally, a process for the preparation of the compounds of the general formula (I) according to the invention has been found, characterised in that in the case in which $R^1$ and $R^2$ have the abovementioned meaning, but do not together form a lactone ring,

[A] aldehydes of the general formula (II)

in which
$R^3$ has the abovementioned meaning, are first reacted with acetoacetic esters of the general formula (III)

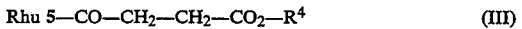

in which
$R^4$ and $R^5$ have the abovementioned meaning, if appropriate with isolation of the corresponding ylidene compounds of the general formula (IV)

in which
$R^3$, $R^4$ and $R^5$ have the abovementioned meaning, and are subsequently reacted either with compounds of the general formula (V)

in which
$R^1$ and $R^2$ have the abovementioned meaning, in the presence of ammonia or ammonium salts, or directly with amino derivatives of the general formula (VI)

in which
R¹ and R² have the abovementioned meaning, if appropriate in the presence of inert organic solvents, or

[B] the aldehydes of the general formula (II) are first reacted with the compounds of the general formula (V), if appropriate with isolation of the ylidene compounds of the general formula (VII)

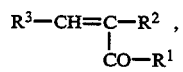 (VII)

in which
R¹, R² and R³ have the abovementioned meaning, and are reacted in a next step with the abovementioned compounds of the general formula (III) in inert solvents, in the presence of ammonia or ammonium salts or directly with enaminocarboxylic acid derivatives of the general formula (VIII)

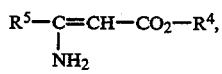 (VIII)

in which
R⁴ and R⁵ have the abovementioned meaning, or in the case in which R¹ and R² together form a lactone ring,

[C] firstly according to the methods mentioned in [A] and [B], compounds of the general formula (Ia)

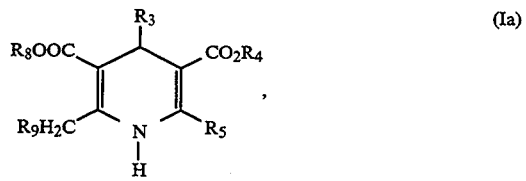 (Ia)

in which
R³, R⁴ and R⁵ have the abovementioned meaning,
R⁸ represents a $C_1$-$C_6$-alkyl radical and
R⁹ represents a leaving group such as, for example, chlorine or acetoxy, are prepared and an acid- or base-catalysed ring closure is added according to known methods, or in the case in which R⁴ does not denote hydrogen,

[D] compounds of the general formula (I) in which R¹, R², R³, R⁴ and R⁵ have the abovementioned meaning and R⁴ represents hydrogen, are reacted with the appropriate alcohols, if appropriate via a reactive acid derivative, the corresponding enantiomers of the esters being obtained by use of the enantiomerically pure carboxylic acids (R⁴=H).

The process according to the invention can be illustrated by way of example by the following reaction scheme:

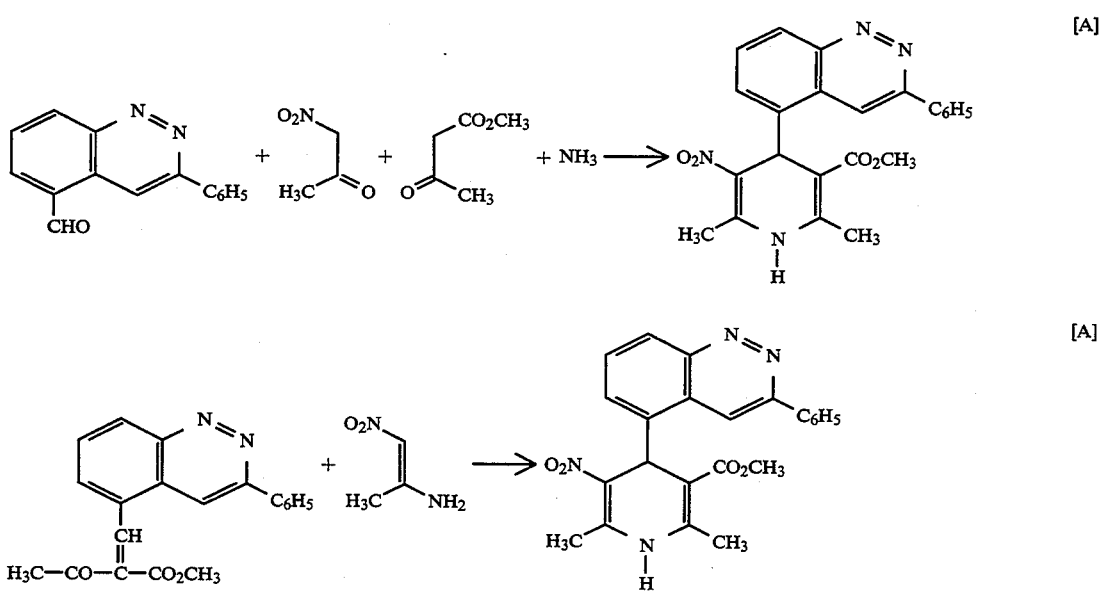

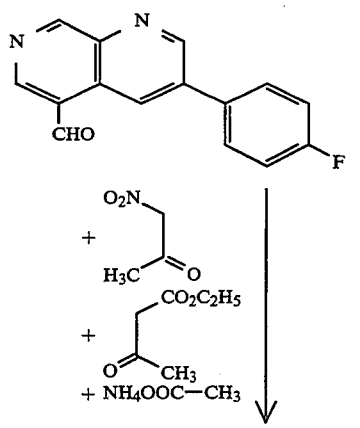
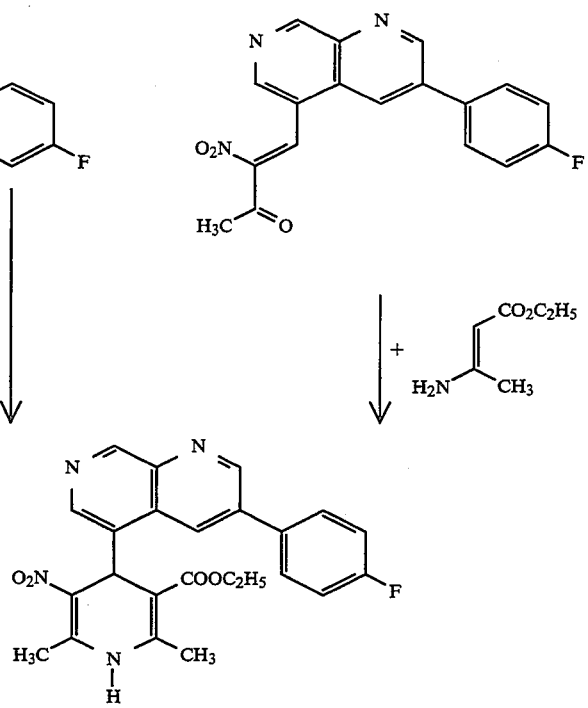
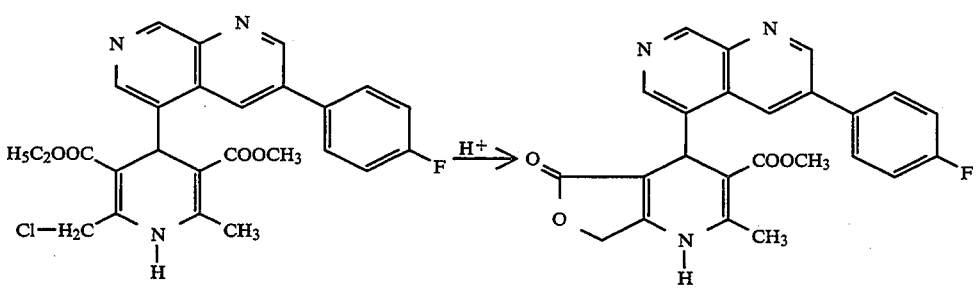

Suitable solvents for processes [A], [B] and [C] are all the inert organic solvents. These preferably include alcohols such as methanol, ethanol, n- or iso-propanol, ethers such as diethyl ether, tetrahydrofuran, dioxane or glycol monomethyl or dimethyl ether, glacial acetic acid, pyridine, dimethylformamide, dimethyl sulphoxide, acetonitrile or hexamethylphosphoramide or toluene.

Suitable solvents for process [D] are the abovementioned solvents with the exception of the alcohols.

The reaction temperature for processes [A], [B], [C] and [D] can be varied within a relatively wide range. In general, the reaction is carried out in a range from 10° C. to 200° C., preferably from 20° C. to 150° C.

The processes can be carried out at normal pressure, elevated pressure or reduced pressure (for example from 0.5 to 5 bar), preferably at normal pressure.

When carrying out the process according to the invention, any desired ratio of the substances involved in the reaction can be used. In general, however, molar amounts of the reactants are used.

To activate the carboxylic acid, suitable reagents are the customary reagents such as inorganic halides, for example thionyl chloride, phosphorus trichloride or phosphorus pentachloride, or carbonyldiimidazole, carbodiimides such as cyclohexylcarbodiimide or 1-cyclohexyl-3-[2-(N-methylmorpholino)ethyl]carbodiimide p-toluenesulphonate or N-hydroxyphthalimide or N-hydroxy-benzotriazole.

Enantiomerically pure forms are obtained, for example, by separating diastereomer mixtures of the compounds of the general formula (I), in which $R^4$ represents an optical ester radical, by a customary method, subsequently preparing the enantiomerically pure carboxylic acids and then optionally converting into the enantiomerically pure dihydropyridines by esterification with appropriate alcohols.

Suitable chiral ester radicals are all the esters of enantiomerically pure alcohols such as, for example, 2-butanol, 1-phenylethanol, lactic acid, lactic acid esters, mandelic acid, mandelic acid esters, 2-aminoalcohols, sugar derivatives and many other enantiomerically pure alcohols.

The diastereomers are in general separated either by fractional crystallisation, by column chromatography or by Craig partition. Which is the optimum process must be decided from case to case, sometimes it is also expedient to use combinations of the individual processes. Separation by crystallisation or Craig partition or a combination of both processes is particularly suitable.

The enantiomerically pure dihydropyridines are preferably esterified in ethers such as diethyl ether or tetrahydrofuran, dimethylformamide, methylene chloride, chloroform, acetonitrile or toluene.

The aldehydes of the general formula (II) are also new and can be prepared by cyclising, in the case in which $R^3$ represents the radical of the formula

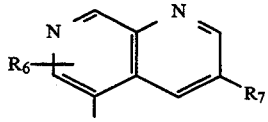

a) substituted pyridines of the general formula (IX)

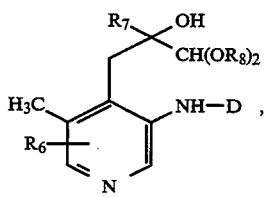

in which
  $R^6$ has the abovementioned meaning, preferably chlorine,
  $R^7$ has the abovementioned meaning,
  D represents a protective group such as, for example, tert-butylcarbonyl and
  $R^8$ represents straight-chain or branched alkyl having up to 4 carbon atoms, first with protonic acids, preferably hydrochloric acid, and subsequent hydrogenation, to give the compounds of the general formula (X)

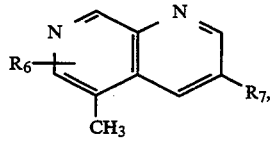

in which
  $R^6$ and $R^7$ have the abovementioned meaning, in inert solvents and in a last step oxidising the methyl group in an organic solvent or naphthalene, preferably naphthalene, and in the case in which $R^3$ represents the radical of the formula

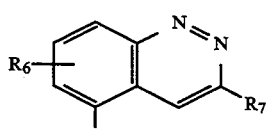

b) cyclising compounds of the general formula (XI)

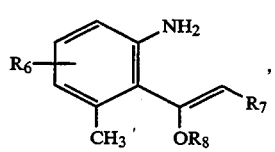

in which
  $R^6$, $R^7$ and $R^8$ have the abovementioned meaning, after hydrolysis, via the diazotised step ($NH_2 \rightarrow N_2^+$), to give compounds of the general formula (XII)

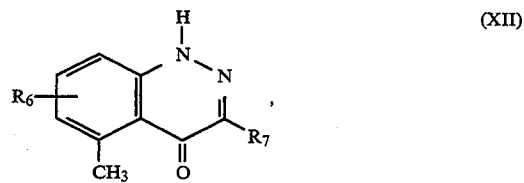

in which
  $R^6$ and $R^7$ have the abovementioned meaning, converting in a second step with $PCl_5/POCl_3$ to compounds of the general formula (XIII)

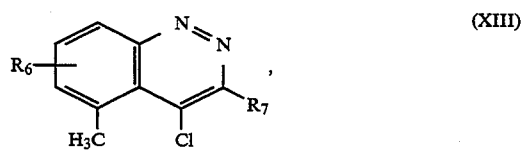

in which
  $R^6$ and $R^7$ have the abovementioned meaning, hydrogenating and subsequently oxidising the methyl group in inert solvents.

The processes according to the invention can be illustrated by way of example by the following reaction scheme:

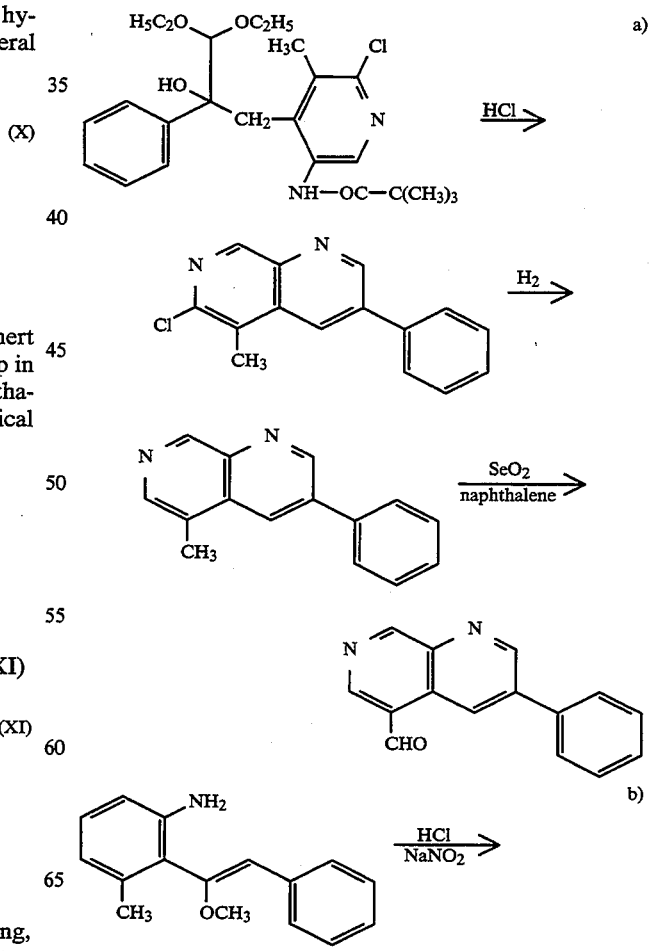

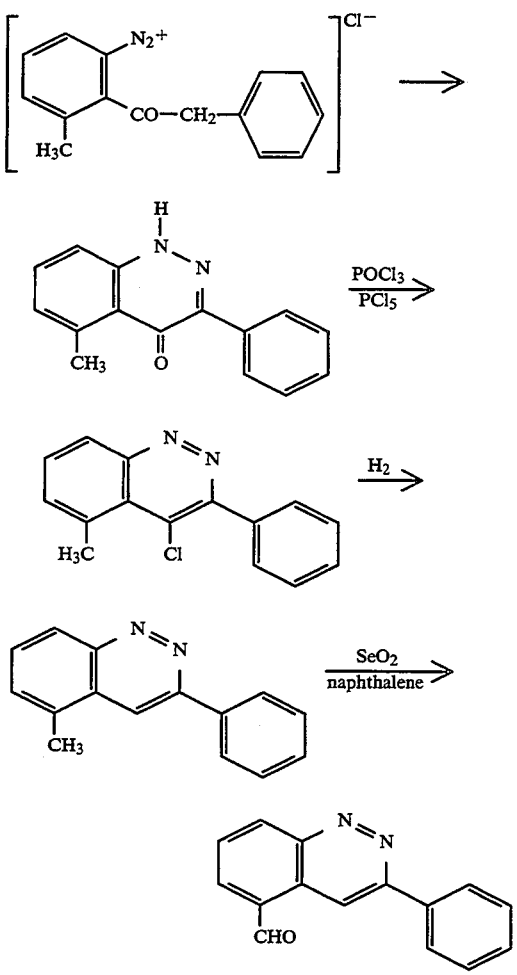

Suitable solvents in this connection are all the inert organic solvents which do not change under the reaction conditions. These preferably include alcohols such as methanol, ethanol, propanol or isopropanol, or ethers such as diethyl ether, dioxane, tetrahydrofuran, glycol dimethyl ether, or diethylene glycol dimethyl ether or amides such as hexamethylphosphoramide or dimethylformamide, or acetic acid as well as methylene chloride, carbon tetrachloride or toluene. It is also possible to use mixtures of the solvents mentioned.

The compounds of the general formulae (X) and (XII) are in general oxidised using oxidising agents such as, for example, chromyl chloride, ceric ammonium nitrate, silver(II) oxide, selenium dioxide or a chromium(VI) oxide in conjunction with acetic anhydride. Selenium dioxide is preferred.

The oxidation can be carried out at normal pressure or elevated or reduced pressure (for example from 0.5 to 5 bar), preferably at normal pressure.

Suitable bases for the individual process steps are those mentioned above, preferably sodium hydroxide and sodium hydrogencarbonate.

The compounds of the general formulae (X), (XII) and (XIII) are new and can be prepared by the above-mentioned process.

The compounds of the general formula (IX) are new and can be prepared by, for example, by first reducing the known compound 2-chloro-3,4-dimethyl-5-nitropyridine [cf. Y. Morisawa et al., J. Med. Chem. 21, 194 (1978)] to give the corresponding 5-amino group by customary methods, for example by hydrogenation with $H_2$/Pd/C in dioxane, subsequently blocking the amino group by reaction with pivaloyl chloride, intermediately deprotonating with n-butyllithium in tetrahydrofuran and in a last step reacting with 2,2-dialkoxyacetophenones.

The compounds of the general formula (XI) are known or can be prepared by customary methods.

The acetoacetic esters of the formula (III) are known or can be prepared by customary methods [cf. D. Borrmann, "Umsetzung von Diketonen mit Alkoholen, Phenolen und Mercaptanen" (Reaction of Diketones with Alcohols, Phenols and Mercaptans), in Houben-Weyl, Methoden der organischen Chemie (Methods of Organic Chemistry), Vol. VIII/4, 230 et seq. (1968)].

The ylidene compounds (Iv) and (VII) are new, but can be prepared by customary methods [cf. H. Dornow and W. Sassenberg, Liebigs Ann. Chem. 602, 14 (1957)].

The aminocrotonic acid derivatives of the formulae (VI) and (VIII) are known or can be prepared by known methods [S. A. Glickman, A. C. Cope, J. Am. Chem. Soc. 67, 1017 (1956)].

The compounds of the general formula (v) are also known [cf. N. Levy, C. W. Scaife, J. Chem. Soc. (London) 1946, 1100; C. D. Hurd, M. E. Nilson, J. Org. Cbem. 20, 927 (1955)].

The above preparation processes are only given for clarification. The preparation of the compounds of the formulae (I) and (II) is not restricted to these processes, but any modification of these processes can be used in the same way for the preparation of the compounds according to the invention.

The compounds according to the invention show an unforeseeable, useful spectrum of pharmacological action. They effect the contractility of the heart and the tone of the smooth musculature. They can therefore be employed in medicaments for effecting pathologically modified blood pressure, as coronary therapeutics and for the treatment of cardiac insufficiency. Moreover, they can be used for the treatment of cardiac arrhythmias, for decreasing the blood sugar, for the detumescence of mucous membranes and for affecting the salt and liquid balance.

The cardiac and vascular actions were found in isolated perfused guinea-pig hearts. For this purpose, the hearts of guinea-pigs of weight 250 to 350 g are used. The animals are killed by a blow to the head, the thorax is opened, and a metal cannula is tied into the exposed aorta. The heart is separated from the thorax with the lungs and connected to the perfusion apparatus via an aorta cannula while perfusing continuously. The lungs are separated at the lung roots. The perfusion medium used is a Krebs-Henseleit solution (1) (118.5 mmol/l of NaCl, 4.75 mmol/l of KCl, 1.19 mmol/l of $KH_2PO_4$, 1.19 mmol/l of $MgSO_4$, 25 mmol/l of $NaHCO_3$, 0.013 mmol/l of $Na_2EDTA$) , whose $CaCl_2$ content is 1.2 mmol/l. 10 mmol/l of glucose is added as the energy-producing substrate. Before perfusion, the solution is filtered free of particles. The solution is aerated with 95% $O_2$, 5% $CO_2$ to maintain pH 7.4. The hearts are perfused at a constant flow rate (10 ml/min) at 32° C. by means of a peristaltic pump.

To measure cardiac function, a liquid-filled latex balloon which is connected to a pressure transducer via a liquid column is introduced through the keft auricle into the left ventricle, and the isovolumetric contractions are recorded on a rapid recorder (Opie, L., J. Physiol. 180 (1965), 529–541). The perfusion pressure is recorded by means of a pressure transducer which is connected to the perfusion system upstream of the heart. Under these conditions, a fall in the perfusion pressure indicates coronary dilatation, an increase or decrease in the left ventricular contraction amplitude indicates a fall or a rise in cardiac contractility. The compounds according to the invention are perfused into the perfusion system at suitable dilutions shortly upstream of the isolated heart.

Substance effects on the contraction amplitude of isolated guinea-pig heart auricles at an active substance concentration of $10^{-4}$ g/l.

| Ex. No. | % change in the ventricular pressure amplitude |
|---|---|
| 8 | +10 |
| 15 | +35 |
| 23 | +28 |

The new active substances can be converted in a known manner into the customary formulations, such as tablets, coated tablets, pills, granules, aerosols, syrups, emulsions, suspensions and solutions, using inert, non-toxic, pharmaceutically suitable excipients or solvents. In this case, the therapeutically active compound should in each case be present in a concentration of about 0.5 to 90% by weight of the total mixture, i.e. in amounts which are sufficient in order to achieve the dosage range indicated.

The formulations are prepared, for example, by extending the active substances with solvents and/or excipients, if appropriate using emulsifiers and/or dispersants, where, for example, in the case of the use of water as a diluent, organic solvents can optionally be used as auxiliary solvents.

Administration is carried out in a customary manner, preferably orally or parenterally, in particular perlingually or intravenously.

In general, it has proved advantageous on intravenous administration to administer amounts of about 0.001 to 1 mg/kg, preferably about 0.01 to 0.5 mg/kg of body weight, to achieve effective results, and on oral administration the dosage is about 0.01 to 20 mg/kg, preferably 0.1 to 10 mg/kg of body weight.

In spite of this, it may be necessary to deviate from the amounts mentioned, in particular depending on the body weight or the type of administration route, on individual behaviour towards the medicament, the manner of its formulation and the time or interval at which administration takes place. Thus, in some cases it may be adequate to manage with less than the abovementioned minimum amount, while in other cases the upper limit mentioned must be exceeded. In the case of the administration of relatively large amounts, it may be advisable to divide these into several individual doses over the course of the day.

Starting Compounds

Example I

3-[2-Chloro-3-methyl-5-pivaloylamino-4-pyridyl]-1,1-diethoxy-2-hydroxy-2-phenylpropane

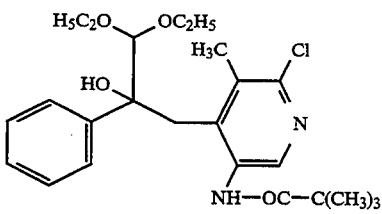

144.3 g (0.6 mol) of 2-chloro-3,4-dimethyl-5-pivaloylaminopyridine are dissolved in 2.9 l of abs. THF and the solution is treated under argon at −78° C. with 127 ml of a 10.4N solution of n-BuLi in n-hexane (1.32 mmol). The mixture is stirred at 0° C. for 3 h, 129.8 ml (0.6 mol) of 2,2-diethoxyacetophenone are slowly added at −78° C. and the mixture is stirred at room temperature overnight. It is then added to water and extracted 3 times with ethyl acetate, dried and concentrated on a rotary evaporator. The purity is sufficient for further reaction. After chromatography, 180.5 g (67%) of the title compound are obtained.

M.p.: 133° C.

Example II

6-Chloro-5-methyl-3-phenyl-1,7-naphthyridine

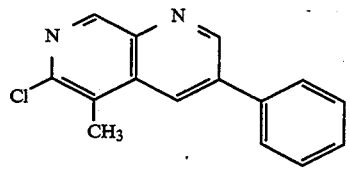

180.5 g (0.4 mol) of finely divided compound from Example I are intensively stirred under reflux for 5 h in 2.6 l of 2N HCl using a mechanical stirrer. The mixture is then neutralised with NaHCOa and extracted several times with ethyl acetate, and the extracts are dried. 37.6 g of the title compound are obtained by crystallisation. Chromatography of the mother liquor (silica gel, toluene→toluene/ethyl acetate 2:1) yields a further 23.14 g of the title compound.

Total yield: 60%

M.p.: 136° C.

Example III

5-Methyl-3-phenyl-1,7-naphthyridine

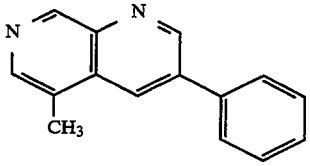

33.7 g (132 mmol) of the compound from Example II are dissolved in 600 ml of ethanol, the solution is treated with 293 ml of 1N NaOH and 10 g of 5% Pd/C and the mixture is immediately hydrogenated in the Parr apparatus at 3 bar for 30 min. It is filtered through kieselguhr and the ethanol content is evaporated in vacuo. The product precipitated in this way is filtered off with suction, washed with plenty of water and then with ether and dried.

Yield: 23.6 g (81.2%)

M.p.: 135–138° C.

Example IV

3-Phenyl-1,7-naphthyridine-5-carboxaldehyde

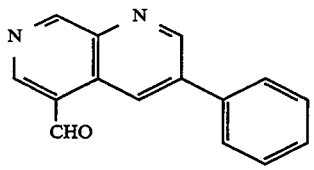

36.2 g (164 mmol) of the compound from Example III are well stirred with 27.4 g of selenium dioxide in 130 g of naphthalene at 180° C. After 5 h, a further 3.65 g of SeO₂ are added and the mixture is stirred for a further 3 h at 200° C. It is allowed to cool and is dissolved in CH₂Cl₂ and the solution is concentrated on a rotary evaporator after addition of 200 g of silica gel. The residue is applied to a large silica gel column and chromatographed (toluene→ethyl acetate).

Yield: 18 g (47%)
M.p.: 148° C.

Example V 1-(1-Amino-3-methyl-2-phenyl)-1-methoxy-2-phenylethene

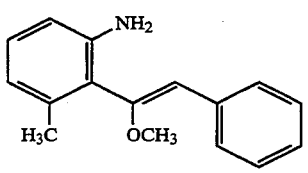

A mixture of 282.3 g (1.21 mol) of 2-iodo-3-methylaniline, 420 ml of butyronitrile, 147.7 g (1.1 mol) of styryl methyl ether, 170 ml of triethylamine and 2.5 g (11 mmol) of Pd(II) acetate is heated at reflux for 8 h. The solution is partly concentrated on a rotary evaporator, mixed with water and extracted 3 times with ethyl acetate. The residue obtained after evaporation of the organic phase is then chromatographed on silica gel.

Yield: 158.8 g (60.3%)
MS (EI): 239 (18%), 135 (28%), 91 (22%), 75 (100%)

Example VI

4-Hydroxy-5-methyl-3-phenylcinnoline

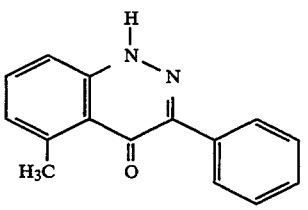

60.5 g (253 mmol) of the compound from Example V are well stirred for 2 h in 1.1 l of 2N HCl and the mixture is boiled under reflux. The solid precipitated in the course of this is processed without isolation by cooling the solution to 0° C. and slowly adding a solution of 17.4 g (252 mmol) of sodium nitrite in 114 ml of water with vigorous stirring. The mixture is then slowly allowed to come to room temperature and is stirred for a further 3 days. The solid is filtered off with suction and washed with ether.

Yield: 27.3 g (46%)
M.p.: 215–217° C.

Example VII

4-Chloro-5-methyl-3-phenylcinnoline

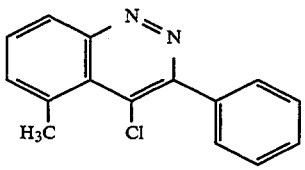

27.3 g (0.116 mol) of the compound from Example VI are boiled under reflux with 18.3 g of PC₅ add 200 ml of POCl₃ for 18 h. The mixture is added to ice with good stirring and extracted with methylene chloride, and the organic phase is washed with saturated NaHCO₃ solution, dried and evaporated in vacuo. 12 g (41% crude yield) of a solid are obtained, which after chromatography has a m.p. of 128° C.

Example VIII

5-Methyl-3-phenylcinnoline

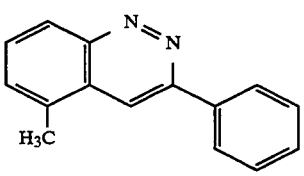

12 g (47.2 mmol) of the compound from Example VII are hydrogenated for several hours at 3 bar in the Parr apparatus in 400 ml of dioxane and 75 ml of 1N NaOH in the presence of 1.5 g of Pd-C (5% strength) with TLC checking. Solid is then filtered off with suction through kieselguhr and the filtrate is concentrated on a rotary evaporator. After chromatography on silica gel (toluene→toluene/ethyl acetate 1:1), 1.8 g (17%) of the pure title compound are obtained.

M.p.: 101° C.

Example IX

3-Phenyl-5-cinnolinecarboxaldehyde

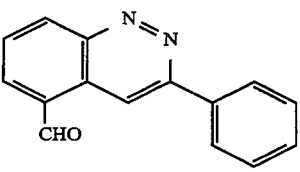

1.65 g (7.5 mmol) of the compound from Example VIII are stirred for 6 h at 200° C. with 1.85 g of selenium dioxide in 17 g of naphthalene. After chromatography on silica gel, 0.75 g (43%) of the title compound is obtained. In some batches, it is necessary to stop the reaction before complete conversion of the starting material, since by-products increasingly occur.

M.p.: 156°–157° C.

Preparation Examples

Example 1

Isopropyl 5-cyano-1,4-dihydro-2,6-dimethyl-4-(3-phenylcinnolin-5-yl)pyridine-3-carboxylate

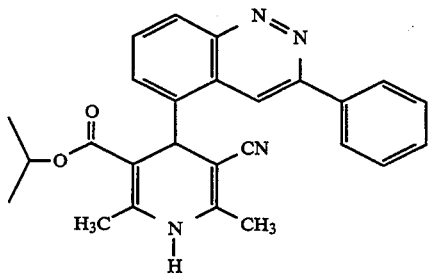

750 mg (3.2 mmol) of 3-phenyl-5-cinnolinecarboxaldehyde, 263 mg (3.2 mmol) of 3-aminocrotononitrile and 457 mg (3.2 mmol) of isopropyl acetoacetate are boiled under reflux for 2.5 days in 25 ml of ethanol. The mixture is concentrated and separated on a silica gel column using toluene/ethyl acetate mixtures. The desired fractions are collected and concentrated. The evaporation residue obtained is crystallised using ether and filtered off with suction. 320 mg of crystals of melting point 200°–202° C. are obtained.

Example 2

Isopropyl 5-cyano-1,4-dihydro-2,6-dimethyl-4-(3-phenyl-1,7-naphthyridin-5-yl)pyridine-3-carboxylate

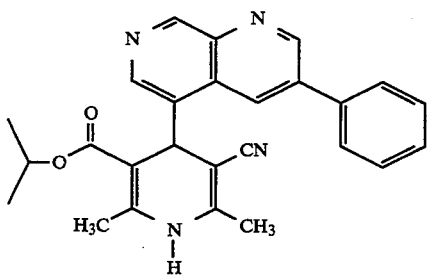

2 g (8.54 mmol) of 3-phenyl-1,7-naphthyridine-5-carboxaidehyde, 701 mg (8.54 mmol) of 3-aminocrotononitrile and 1.22 g (8.54 mmol) of isopropyl acetoacetate are boiled under reflux for 3 days in 25 ml of ethanol. The mixture is concentrated and separated on a silica gel column using toluene/ethyl acetate mixtures. The desired fractions are collected and concentrated. The evaporation residue obtained is crystallised using ether and filtered off with suction. 573 mg of crystals of melting point 192° C. are obtained.

The compounds shown in Table 1 are prepared in analogy to the procedure of Example 1:

TABLE 1

| Ex. No. | $R^1$ | $R^2$ | $R^4$ | M.p. °C./$R_f$/enantiomer |
|---|---|---|---|---|
| 3 | —$CH_3$ | —CN | —$CH(CH_3)_2$ | 202 |
| 4 | —$CH_3$ | —CN | —$C_2H_5$ | 190 |
| 5 | | | —$CH(CH_3)_2$ | 150 |
| 6 | —$CH_3$ | —$NO_2$ | —$C_2H_5$ | 218 |
| 7 | —$CH_3$ | —CN | —$CH_2$—$CF_3$ | 196 |
| 8 | —$CH_3$ | —CN | n-$C_3H_7$ | 190 |
| 9 | —$CH_3$ | —CN | —$CH(CH_3)_2$ | 226–227/enantiomer 1 |
| 10 | —$CH_3$ | —CN | —$CH(CH_3)_2$ | 226–227/enantiomer 2 |

Compounds shown in Table 2 are prepared in analogy to the procedure of Example 2:

TABLE 2

| Ex. No. | $R^1$ | $R^2$ | $R^4$ | $R^5$ | M.p. °C./$R_f$/Enantiomer |
|---|---|---|---|---|---|
| 11 | —$CH_3$ | —CN | —$CH(CH_3)_2$ | —$CH_3$ | 192 |
| 12 | | | —$C_2H_5$ | —$CH_3$ | 248 |
| 13 | —$CH_3$ | —$NO_2$ | —$C_2H_5$ | —$CH_3$ | 258 |
| 14 | —$CH_3$ | —CN | n-$C_3H_7$ | —$CH_3$ | 212 |

TABLE 2-continued

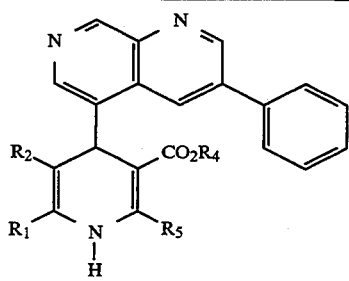

| Ex. No. | R¹ | R² | R⁴ | R⁵ | M.p. °C./$R_f$/Enantiomer |
|---|---|---|---|---|---|
| 15 | | 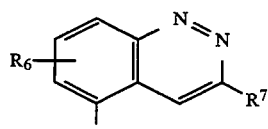 | —CH(CH₃)₂ | —CH₃ | 160 |
| 16 | —CH₃ | —CO₂—CH(CH₃)₂ | —(CH₂)₂OCH₃ | —CH₃ | 193 |
| 17 | —CH₃ | —NO₂ | —CH(CH₃)₂ | —CH₃ | 255 |
| 18 | | 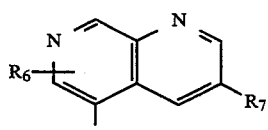 | —CH₃ | —CH₃ | 250 |
| 19 | —CH₃ | —NO₂ | —CH₃ | —CH₃ | 255 |
| 20 | —CH₃ | —CN | n-C₃H₇ | —CH₃ | 224/(+)-enantiomer |
| 21 | —CH₃ | —CN | —CH(CH₃)₂ | —CH₃ | oil/(+)-enantiomer |
| 22 | —CH₃ | —CN | —CH(CH₃)₂ | —CH₃ | oil/(−)-enantiomer |
| 23 | —CH₃ | —CN | n-C₃H₇ | —CH₃ | 219/(−)-enantiomer |
| 24 | —CH₃ | —CN | —CH₂—CF₃ | —CH₃ | 199 |
| 25 | —CH₃ | —CN | —C₂H₅ | —CH₃ | 252 |

We claim:

1. An aldehyde of the formula

R³—CHO in which

R³ represents a heterocyclic radical of the formula

or

in which

R⁶ denotes hydrogen, halogen or straight-chain or branched alkyl or alkoxy each having up to 8 carbon atoms, R⁷ represents pyridyl or thienyl, or aryl having 6 to 10 carbon atoms, which is optionally substituted up to 2 times by identical or different substituents wherein the substituents are halogen, nitro, cyano, trifluoromethyl, trifluoromethoxy, trifluoromethylthio, straight-chain or branched alkyl, alkoxy or alkoxycarbonyl each having up to 8 carbon atoms or carboxyl.

2. A compound according to claim 1 wherein such compound is 3-phenyl-1,7-naphthyridine-5-carbaldehyde of the formula

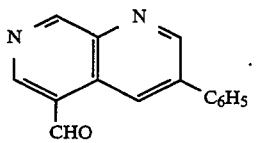

3. A compound according to claim 1 wherein such compound is 3-phenyl-cinnoline-5-carboxaldehyde of the formula

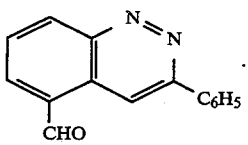

* * * * *